US00PP30256P2

(12) United States Plant Patent
Widdowson

(10) Patent No.: US PP30,256 P2
(45) Date of Patent: Feb. 26, 2019

(54) ***GAURA* PLANT NAMED 'GBAWH02-1'**

(50) Latin Name: *Gaura lindheimeri*
Varietal Denomination: GBAWH02-1

(71) Applicant: Nadine Widdowson, Dereham (GB)

(72) Inventor: Nadine Widdowson, Dereham (GB)

(73) Assignee: FloraNova Ltd, Norfolk (GB)

( * ) Notice: Subject to any disclaimer, the term of this patent is extended or adjusted under 35 U.S.C. 154(b) by 0 days.

(21) Appl. No.: 15/731,935

(22) Filed: Aug. 25, 2017

(51) Int. Cl.
*A01H 5/02* (2018.01)

(52) U.S. Cl.
USPC ..... Plt./432
CPC ..... *A01H 5/02* (2013.01)

(58) Field of Classification Search
USPC ..... Plt./432
See application file for complete search history.

*Primary Examiner* — Anne Marie Grunberg
(74) *Attorney, Agent, or Firm* — Cassandra Bright

(57) ABSTRACT

A new and distinct cultivar of *Gaura lindheimeri* plant named 'GBAWH02-1' is disclosed, characterized by dense, compact plants. Flowering begins early and flower petals are clear white. The new variety is a *Gaura*, and is normally used as an ornamental garden or container plant.

1 Drawing Sheet

Latin name of the genus and species: *Gaura lindheimeri.*
Variety denomination: 'GBAWH02-1'.

BACKGROUND OF THE INVENTION

The new cultivar is the product of a breeding program, with the object to develop floriferous semi-compact *Gaura* varieties for commercial applications. The new variety originated from a crossing of the seed parent, an unnamed proprietary *Gaura lindheimeri* with the pollen parent, also an unnamed, unpatented proprietary *Gaura lindheimeri*. The cross resulting in the new variety was made June 2010 at a research greenhouse in Foxley, the United Kingdom.

The new variety was selected by the inventor, Nadine Widdowson, during May of 2011 at a research nursery in greenhouse in Foxley, the United Kingdom. After identifying the new variety as a potentially interesting selection, the inventor continued confidential testing and propagation of 'GBAWH02-1' assessing stability of the unique characteristics of this variety.

Asexual reproduction of the new cultivar 'GBAWH02-1' was first performed in Victoria, Australia by vegetative terminal cuttings in October of 2011. 'GBAWH02-1' has since produced more than 5 generations by vegetative cuttings and has shown that the unique features of this cultivar are stable and reproduced true to type.

SUMMARY OF THE INVENTION

The cultivar 'GBAWH02-1' has not been observed under all possible environmental conditions. The phenotype may vary somewhat with variations in environment such as temperature, day length, and light intensity, without, however, any variance in genotype.

The following traits have been repeatedly observed and are determined to be the unique characteristics of 'GBAWH02-1'. These characteristics in combination distinguish 'GBAWH02-1' as a new and distinct *Gaura lindheimeri* cultivar:

1. Early flowering plants.
2. Compact plant habit.
3. Clear white flower petals.
4. Dense branching.

PARENT COMPARISON

Plants of the new cultivar 'GBAWH02-1' are similar to the seed parent in most horticultural characteristics. The new variety, however, differs in the following:

1. The new variety produces white flowers compared to the pink flower of the seed parent
2. The seed parent is more compact in plant habit.

Plants of the new cultivar 'GBAWH02-1' are similar to the pollen parent in most horticultural characteristics. The new variety, however, differs in the following:

1. The new variety is much shorter than the pollen parent.
2. Plants of the new variety are denser with more branches.

COMMERCIAL COMPARISON

Plants of the new cultivar 'GBAWH02-1' are similar to plants of the commercial variety, *Gaura lindheimeri* 'GBAWH02-0' U.S. Plant Pat. No. 25,720, in most horticultural characteristics. However, plants of the new cultivar 'GBAWH02-1' differ in the following:

1. Plants of the new variety are more vigorous and taller.
2. Plants of the new variety begin flowering earlier than plants of this comparator.

Plants of the new cultivar 'GBAWH02-1' are similar to plants of the commercial variety, *Gaura lindheimeri* 'Whirling Butterflies', unpatented, in most horticultural characteristics. However, plants of the new cultivar 'GBAWH02-1' differ in the following:

1. Plants of the new variety are shorter than plants of this comparator.
2. Plants of the new variety begin flowering earlier than plants of this comparator.

BRIEF DESCRIPTION OF THE PHOTOGRAPH

The accompanying photograph illustrates in full color a typical plant of 'GBAWH02-1' grown in a greenhouse. The pot size is a commercial 8 inch pot. The plant shown is approximately 16 weeks old. The photograph was taken using conventional techniques and although colors may appear different from actual colors due to light reflectance it is as accurate as possible by conventional photographic techniques.

DETAILED BOTANICAL DESCRIPTION

In the following description, color references are made to The Royal Horticultural Society Colour Chart 2007 except where general terms of ordinary dictionary significance are used. The following observations and measurements describe 'GBAWH02-1' plants grown in a commercial controlled greenhouse in Santa Paula, Calif. Temperatures ranged from 15° C. to 28° C. during the day and 18° C. to 22° C. at night. No artificial light, photoperiodic treatments or chemical treatments were given to the plants. Measurements and numerical values represent averages of typical plant types.

Botanical classification: *Gaura lindheimeri* 'GBAWH02-1'.

PROPAGATION

Time to initiate roots: 15 to 20 days at approximately 20° C.

Root description: Fibrous, colored near RHS Greyed-Orange 165D.

PLANT

Growth habit: Upright perennial.

Pot size of plant described: 1 gallon.

Height: 55 cm.

Plant spread: 50 cm.

Growth rate: Rapid.

Branching characteristics: Basal branching, or nearly at soil level. No lateral produced above 1.5 cm above soil level.

Length of primary branches: Approximately 12 to 20 cm.

Diameter of branches: Approximately 2 mm.

Quantity of primary branches: Average 50.

Characteristics of primary lateral branches:

- *Form*.—Irregular round, some flat sides.
- *Color*.—Near RHS Yellow-Green 144B.
- *Texture*.—Scant pubescence.
- *Strength*.—Strong, somewhat flexible.

Internode length: Average 1.0 to 1.8 cm.

FOLIAGE

Leaf:

- *Arrangement*.—Alternate, simple.
- *Average length*.—3.5 cm.
- *Average width*.—1.0 cm.
- *Shape of blade*.—Elliptic.
- *Apex*.—Acute.
- *Base*.—Attenuate.
- *Margin*.—Nearly entire, infrequent shallow serrations present on some leaves.
- *Texture of top surface*.—Scant pubescence visible under magnification.
- *Texture of bottom surface*.—Glabrous.
- *Aspect*.—Flat to very slightly undulating.
- *Color*.—Young foliage upper side: Near RHS Green 137A. Young foliage under side: Near RHS Green 137A. Mature foliage upper side: Near RHS Green 137A. Mature foliage under side: Near RHS Green 137A.
- *Venation*.—Type: Pinnate. Venation color upper side: Near RHS Green 137D. Venation color under side: Near RHS Green 137D.
- *Petiole*.—Sessile.

FLOWER

Natural flowering season: Spring through Summer.

Inflorescence and flower type and habit: Single zygomorphic flowers produced on terminal and axillary racemes.

Persistent or self-cleaning: Self-Cleaning.

Bud:

- *Shape*.—Cylindric.
- *Length*.—1.7 cm.
- *Diameter*.—0.3 cm.
- *Color*.—Near RHS Greyed-Purple 187C. Apex near Yellow-Green 144A. Base near Greyed-Purple 187B.

Raceme:

- *Diameter*.—Average 7 cm.
- *Length*.—Average range 10 to 22 cm.
- *Flowers per raceme*.—8 to 16.

Flower size:

- *Diameter*.—Average 3.5 cm.
- *Length*.—Average 1.5 cm excluding stamens, 3.0 including stamens.

Corolla/petals:

- *Quantity of petals*.—4.
- *Arrangement*.—Asymmetrical whorl.
- *Petal length*.—2.0 cm.
- *Petal width*.—1.0 cm.
- *Corolla tube length*.—1.2 cm.
- *Corolla tube diameter*.—0.2 cm.
- *Texture*.—Glabrous.
- *Petal apex*.—Broad acute.
- *Petal base*.—Attenuate.
- *Petal shape*.—Broad spatulate.
- *Margin*.—Entire.
- *Aspect*.—Upwardly cupped to slightly undulating.

Petal color:

- *When opening*.—Upper surface: Near RHS White N155D. Lower surface: Near RHS White N155D.
- *Fully opened*.—Upper surface: Near RHS White N155. Lower surface: Near RHS White N155D.

Outer corolla tube color: Near RHS Red-Purple 60A.

Inner corolla tube color: Near RHS Red-Purple 60D.

Calyx/sepals:

- *Quantity per flower*.—4.
- *Shape*.—Linear.
- *Length*.—1.1 cm.
- *Width*.—0.3 cm.
- *Apex*.—Acute.
- *Base*.—Truncate.
- *Margin*.—Entire.
- *Texture*.—Pubescent lower surface, glabrous upper surface.
- *Aspect*.—Undulating and strongly reflexed back.
- *Color*.—Upper Surface: Near RHS Green-White 157B, base heavily flushed Red-Purple 58D, apex 61A. Lower Surface: Near RHS Green-White 157B, base heavily flushed Red-Purple 58D, apex 61A.

Peduncle:

*Length*.—Average range 4 to 11 cm.

*Diameter*.—Approximately 0.2 cm.

*Color*.—Near RHS Greyed-Purple N186C.

*Orientation*.—Upright.

*Texture*.—Glabrous.

*Strength*.—Strong and flexible.

Pedicel: Not present, directly attached by corolla tube to Peduncle.

Fragrance: None detected.

REPRODUCTIVE ORGANS

Stamens:

*Number*.—8.

*Filament length*.—Approximately 1.5 cm.

Anthers:

*Shape*.—Linear.

*Length*.—Approximately 0.5 cm.

*Color*.—Near RHS Greyed-Yellow 161B.

*Pollen*.—Color: Near RHS Greyed-Yellow 161D. Quantity: Scant.

Pistil:

*Number*.—1.

*Length*.—3.0 cm.

*Style*.—Length: 1.8 cm. Color: Near RHS White N155D.

*Stigma*.—Shape: Bi lobed. Color: Near RHS Green-White 157A.

*Ovary*.—Ovary Color: Near RHS Yellow-Green 145A. Ovary Length: Approximately 1.2 cm. Ovary diameter: Approximately 0.1 cm. Ovary shape: Linear.

OTHER CHARACTERISTICS

Seeds and fruits: Not observed to date.

Disease/pest resistance: Neither resistance nor susceptibility to diseases or pests has been observed in this variety.

Temperature tolerance: The new variety tolerates temperatures from approximately −5° to 35-8° C.

What is claimed is:

1. A new and distinct cultivar of *Gaura* plant named 'GBAWH02-1' as herein illustrated and described.

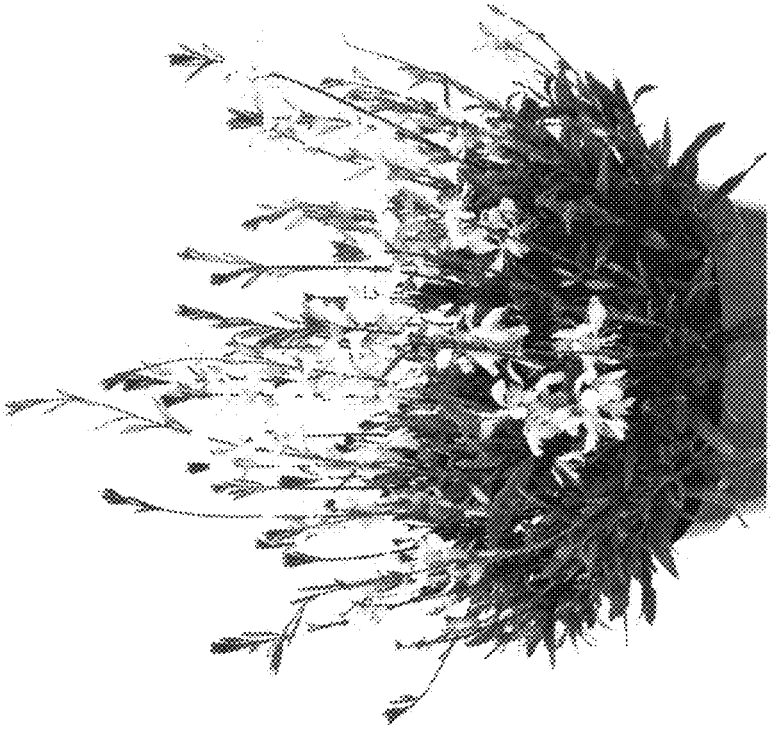

* * * * *